US007608430B2

(12) United States Patent
Karow et al.

(10) Patent No.: US 7,608,430 B2
(45) **Date of Patent: *Oct. 27, 2009**

(54) INTERFERON-γ ANTAGONISTS AND THERAPEUTIC USES THEREOF

(75) Inventors: Margaret Karow, Camarillo, CA (US); Prerna Sharma, Stamford, CT (US)

(73) Assignee: Regeneron Pharmaceuticals, Inc., Tarrytown, NY (US)

(*) Notice: Subject to any disclaimer, the term of this patent is extended or adjusted under 35 U.S.C. 154(b) by 201 days.

This patent is subject to a terminal disclaimer.

(21) Appl. No.: 11/481,614

(22) Filed: Jul. 6, 2006

(65) Prior Publication Data

US 2007/0020283 A1 Jan. 25, 2007

Related U.S. Application Data

(60) Provisional application No. 60/697,689, filed on Jul. 8, 2005.

(51) Int. Cl.

| | |
|---|---|
| ***C12P 21/04*** | (2006.01) |
| ***C12N 15/00*** | (2006.01) |
| ***C12N 5/00*** | (2006.01) |
| ***C07K 14/435*** | (2006.01) |
| ***C07H 21/04*** | (2006.01) |

(52) U.S. Cl. .................. 435/69.7; 530/350; 435/320.1; 435/325; 536/23.4

(58) Field of Classification Search ....................... None
See application file for complete search history.

(56) References Cited

U.S. PATENT DOCUMENTS

| | | | | |
|---|---|---|---|---|
| 5,221,789 | A * | 6/1993 | Novick et al. | 530/350 |
| 6,287,853 | B1 * | 9/2001 | Pestka et al. | 435/320.1 |
| 6,472,179 | B2 * | 10/2002 | Stahl et al. | 435/69.7 |
| 6,558,661 | B1 * | 5/2003 | Ashkenazi et al. | 424/85.4 |
| 7,083,950 | B2 * | 8/2006 | Stahl et al. | 435/69.7 |

FOREIGN PATENT DOCUMENTS

| | | |
|---|---|---|
| EP | 0614981 A1 | 9/1994 |
| EP | 0393502 B1 | 12/1995 |
| WO | WO 95/05847 | 3/1995 |
| WO | WO 95/16036 | 6/1995 |

OTHER PUBLICATIONS

Jouanguy, E., H., et al., (2000) J. Clin. Invest., 105(10):1429-1436.
Fountoulakis, M., et al., (1995) J. Bio. Chem., 270(8):3958-3964.
Shankaran, V., et al., IFN gamma Receptor in Cytokine Database, Oppenheim and Feldmann editors, London:Academics, 2000:1819-1836.

* cited by examiner

*Primary Examiner*—Marianne P Allen
(74) *Attorney, Agent, or Firm*—Valeta Gregg, Esq.; Izumi Yokoyama, Esq.

(57) ABSTRACT

Polypeptides and multimeric polypeptides capable of binding interferon γ which are useful therapeutically in methods of treating interferon γ-related conditions or diseases.

10 Claims, No Drawings

SEQUENCE LISTING

```
<160> NUMBER OF SEQ ID NOS: 15

<210> SEQ ID NO 1
<211> LENGTH: 1467
<212> TYPE: DNA
<213> ORGANISM: Homo sapiens

<400> SEQUENCE: 1
```

-continued

```
atggctctcc tctttctcct accccttgtc atgcagggtg tgagcagggc tgagatgggc      60

accgcggatc tggggccgtc ctcagtgcct acaccaacta atgttacaat tgaatcctat     120

aacatgaacc ctatcgtata ttgggagtac cagatcatgc cacaggtccc tgtttttacc     180

gtagaggtaa agaactatgg tgttaagaat tcagaatgga ttgatgcctg catcaatatt     240

tctcatcatt attgtaatat ttctgatcat gttggtgatc catcaaattc tctttgggtc     300

agagttaaag ccagggttgg acaaaaagaa tctgcctatg caaagtcaga agaatttgct     360

gtatgccgag atggaaaaat tggaccacct aaactggata tcagaaagga ggagaagcaa     420

atcatgattg acatatttca cccttcagtt tttgtaaatg gagacgagca ggaagtcgat     480

tatgatcccg aaactacctg ttacattagg gtgtacaatg tgtatgtgag aatgaacgga     540

agtgagatcc agtataaaat actcacgcag aaggaagatg attgtgacga gattcagtgc     600

cagttagcga ttccagtatc ctcactgaat tctcagtact gtgtttcagc agaaggagtc     660

ttacatgtgt ggggtgttac aactgaaaag tcaaaagaag tttgtattac cattttcaat     720

agcagtataa aaggttctct ttggattcca gttgttgctg ctttactact ctttctagtg     780

cttagcctgg tattcatctg tttttatatt aagaaaatta atccattgaa ggaaaaaagc     840

ataatattac ccaagtcctt gatctctgtg gtaagaagtg ctactttaga gacaaaacct     900

gaatcaaaat atgtatcact catcacgtca taccagccat tttccttaga aaaggaggtg     960

gtctgtgaag agccgttgtc tccagcaaca gttccaggca tgcataccga agacaatcca    1020

ggaaaagtgg aacatacaga agaactttct agtataacag aagtggtgac tactgaagaa    1080

aatattcctg acgtggtccc gggcagccat ctgactccaa tagagagaga gagttcttca    1140

cctttaagta gtaaccagtc tgaacctggc agcatcgctt taaactcgta tcactccaga    1200

aattgttctg agagtgatca ctccagaaat ggttttgata ctgattccag ctgtctggaa    1260

tcacatagct ccttatctga ctcagaattt cccccaaata ataaaggtga aataaaaaca    1320

gaaggacaag agctcataac cgtaataaaa gcccccacct cctttggtta tgataaacca    1380

catgtgctag tggatctact tgtggatgat agcggtaaag agtccttgat tggttataga    1440

ccaacagaag attccaaaga attttca                                        1467
```

```
<210> SEQ ID NO 2
<211> LENGTH: 489
<212> TYPE: PRT
<213> ORGANISM: Homo sapiens

<400> SEQUENCE: 2

Met Ala Leu Leu Phe Leu Leu Pro Leu Val Met Gln Gly Val Ser Arg
1               5                   10                  15

Ala Glu Met Gly Thr Ala Asp Leu Gly Pro Ser Ser Val Pro Thr Pro
            20                  25                  30

Thr Asn Val Thr Ile Glu Ser Tyr Asn Met Asn Pro Ile Val Tyr Trp
        35                  40                  45

Glu Tyr Gln Ile Met Pro Gln Val Pro Val Phe Thr Val Glu Val Lys
    50                  55                  60

Asn Tyr Gly Val Lys Asn Ser Glu Trp Ile Asp Ala Cys Ile Asn Ile
65                  70                  75                  80

Ser His His Tyr Cys Asn Ile Ser Asp His Val Gly Asp Pro Ser Asn
                85                  90                  95

Ser Leu Trp Val Arg Val Lys Ala Arg Val Gly Gln Lys Glu Ser Ala
            100                 105                 110
```

-continued

```
Tyr Ala Lys Ser Glu Glu Phe Ala Val Cys Arg Asp Gly Lys Ile Gly
        115                 120                 125

Pro Pro Lys Leu Asp Ile Arg Lys Glu Glu Lys Gln Ile Met Ile Asp
    130                 135                 140

Ile Phe His Pro Ser Val Phe Val Asn Gly Asp Glu Gln Glu Val Asp
145                 150                 155                 160

Tyr Asp Pro Glu Thr Thr Cys Tyr Ile Arg Val Tyr Asn Val Tyr Val
                165                 170                 175

Arg Met Asn Gly Ser Glu Ile Gln Tyr Lys Ile Leu Thr Gln Lys Glu
            180                 185                 190

Asp Asp Cys Asp Glu Ile Gln Cys Gln Leu Ala Ile Pro Val Ser Ser
        195                 200                 205

Leu Asn Ser Gln Tyr Cys Val Ser Ala Glu Gly Val Leu His Val Trp
    210                 215                 220

Gly Val Thr Thr Glu Lys Ser Lys Glu Val Cys Ile Thr Ile Phe Asn
225                 230                 235                 240

Ser Ser Ile Lys Gly Ser Leu Trp Ile Pro Val Val Ala Ala Leu Leu
                245                 250                 255

Leu Phe Leu Val Leu Ser Leu Val Phe Ile Cys Phe Tyr Ile Lys Lys
            260                 265                 270

Ile Asn Pro Leu Lys Glu Lys Ser Ile Ile Leu Pro Lys Ser Leu Ile
        275                 280                 285

Ser Val Val Arg Ser Ala Thr Leu Glu Thr Lys Pro Glu Ser Lys Tyr
    290                 295                 300

Val Ser Leu Ile Thr Ser Tyr Gln Pro Phe Ser Leu Glu Lys Glu Val
305                 310                 315                 320

Val Cys Glu Glu Pro Leu Ser Pro Ala Thr Val Pro Gly Met His Thr
                325                 330                 335

Glu Asp Asn Pro Gly Lys Val Glu His Thr Glu Glu Leu Ser Ser Ile
            340                 345                 350

Thr Glu Val Val Thr Thr Glu Glu Asn Ile Pro Asp Val Val Pro Gly
        355                 360                 365

Ser His Leu Thr Pro Ile Glu Arg Glu Ser Ser Ser Pro Leu Ser Ser
    370                 375                 380

Asn Gln Ser Glu Pro Gly Ser Ile Ala Leu Asn Ser Tyr His Ser Arg
385                 390                 395                 400

Asn Cys Ser Glu Ser Asp His Ser Arg Asn Gly Phe Asp Thr Asp Ser
                405                 410                 415

Ser Cys Leu Glu Ser His Ser Ser Leu Ser Asp Ser Glu Phe Pro Pro
            420                 425                 430

Asn Asn Lys Gly Glu Ile Lys Thr Glu Gly Gln Glu Leu Ile Thr Val
        435                 440                 445

Ile Lys Ala Pro Thr Ser Phe Gly Tyr Asp Lys Pro His Val Leu Val
    450                 455                 460

Asp Leu Leu Val Asp Asp Ser Gly Lys Glu Ser Leu Ile Gly Tyr Arg
465                 470                 475                 480

Pro Thr Glu Asp Ser Lys Glu Phe Ser
                485
```

<210> SEQ ID NO 3
<211> LENGTH: 1011
<212> TYPE: DNA
<213> ORGANISM: homo sapiens

<400> SEQUENCE: 3

-continued

```
atgcgaccga cgctgctgtg gtcgctgctg ctgctgctcg gagtcttcgc cgccgccgcc     60

gcggccccgc cagaccctct ttcccagctg cccgctcctc agcacccgaa gattcgcctg    120

tacaacgcag agcaggtcct gagttgggag ccagtggccc tgagcaatag cacgaggcct    180

gttgtctacc aagtgcagtt taaatacacc gacagtaaat ggttcacggc cgacatcatg    240

tccatagggg tgaattgtac acagatcaca gcaacagagt gtgacttcac tgccgccagt    300

ccctcagcag gcttcccaat ggatttcaat gtcactctac gccttcgagc tgagctggga    360

gcactccatt ctgcctgggt gacaatgcct tggtttcaac actatcggaa tgtgactgtc    420

gggcctccag aaaacattga ggtgacccca ggagaaggct ccctcatcat caggttctcc    480

tctccctttg acatcgctga tacctccacg gccttttttt gttattatgt ccattactgg    540

gaaaaaggag gaatccaaca ggtcaaaggc cctttcagaa gcaactccat ttcattggat    600

aacttaaaac cctccagagt gtactgttta caagtccagg cacaactgct ttggaacaaa    660

agtaacatct ttagagtcgg gcatttaagc aacatatctt gctacgaaac aatggcagat    720

gcctccactg agcttcagca agtcatcctg atctccgtgg gaacattttc gttgctgtcg    780

gtgctggcag gagcctgttt cttcctggtc ctgaaatata gaggcctgat taaatactgg    840

tttcacactc caccaagcat cccattacag atagaagagt atttaaaaga cccaactcag    900

cccatcttag aggccttgga caaggacagc tcaccaaagg atgacgtctg ggactctgtg    960

tccattatct cgtttccgga aaaggagcaa gaagatgttc tccaaacgct t            1011
```

<210> SEQ ID NO 4
<211> LENGTH: 337
<212> TYPE: PRT
<213> ORGANISM: Homo sapiens

<400> SEQUENCE: 4

```
Met Arg Pro Thr Leu Leu Trp Ser Leu Leu Leu Leu Leu Gly Val Phe
 1               5                  10                  15

Ala Ala Ala Ala Ala Ala Pro Pro Asp Pro Leu Ser Gln Leu Pro Ala
            20                  25                  30

Pro Gln His Pro Lys Ile Arg Leu Tyr Asn Ala Glu Gln Val Leu Ser
        35                  40                  45

Trp Glu Pro Val Ala Leu Ser Asn Ser Thr Arg Pro Val Val Tyr Gln
    50                  55                  60

Val Gln Phe Lys Tyr Thr Asp Ser Lys Trp Phe Thr Ala Asp Ile Met
65                  70                  75                  80

Ser Ile Gly Val Asn Cys Thr Gln Ile Thr Ala Thr Glu Cys Asp Phe
                85                  90                  95

Thr Ala Ala Ser Pro Ser Ala Gly Phe Pro Met Asp Phe Asn Val Thr
            100                 105                 110

Leu Arg Leu Arg Ala Glu Leu Gly Ala Leu His Ser Ala Trp Val Thr
        115                 120                 125

Met Pro Trp Phe Gln His Tyr Arg Asn Val Thr Val Gly Pro Pro Glu
    130                 135                 140

Asn Ile Glu Val Thr Pro Gly Glu Gly Ser Leu Ile Ile Arg Phe Ser
145                 150                 155                 160

Ser Pro Phe Asp Ile Ala Asp Thr Ser Thr Ala Phe Phe Cys Tyr Tyr
                165                 170                 175

Val His Tyr Trp Glu Lys Gly Gly Ile Gln Gln Val Lys Gly Pro Phe
            180                 185                 190
```

-continued

```
Arg Ser Asn Ser Ile Ser Leu Asp Asn Leu Lys Pro Ser Arg Val Tyr
        195                 200                 205

Cys Leu Gln Val Gln Ala Gln Leu Leu Trp Asn Lys Ser Asn Ile Phe
    210                 215                 220

Arg Val Gly His Leu Ser Asn Ile Ser Cys Tyr Glu Thr Met Ala Asp
225                 230                 235                 240

Ala Ser Thr Glu Leu Gln Gln Val Ile Leu Ile Ser Val Gly Thr Phe
                245                 250                 255

Ser Leu Leu Ser Val Leu Ala Gly Ala Cys Phe Phe Leu Val Leu Lys
            260                 265                 270

Tyr Arg Gly Leu Ile Lys Tyr Trp Phe His Thr Pro Pro Ser Ile Pro
        275                 280                 285

Leu Gln Ile Glu Glu Tyr Leu Lys Asp Pro Thr Gln Pro Ile Leu Glu
    290                 295                 300

Ala Leu Asp Lys Asp Ser Ser Pro Lys Asp Asp Val Trp Asp Ser Val
305                 310                 315                 320

Ser Ile Ile Ser Phe Pro Glu Lys Glu Gln Glu Asp Val Leu Gln Thr
                325                 330                 335

Leu


<210> SEQ ID NO 5
<211> LENGTH: 29
<212> TYPE: PRT
<213> ORGANISM: Artificial Sequence
<220> FEATURE:
<223> OTHER INFORMATION: Synthetic

<400> SEQUENCE: 5

Met His Arg Pro Arg Arg Arg Gly Thr Arg Pro Pro Pro Leu Ala Leu
 1               5                  10                  15

Leu Ala Ala Leu Leu Leu Ala Ala Arg Gly Ala Asp Ala
            20                  25


<210> SEQ ID NO 6
<211> LENGTH: 2055
<212> TYPE: DNA
<213> ORGANISM: Artificial Sequence
<220> FEATURE:
<223> OTHER INFORMATION: Synthetic

<400> SEQUENCE: 6

atggtgctcc tctttctcct accccttgtc atgcagggtg tgagcagggc tgagatgggc      60

accgcggatc tggggccgtc ctcagtgcct acaccaacta atgttacaat tgaatcctat     120

aacatgaacc ctatcgtata ttgggagtac cagatcatgc cacaggtccc tgtttttacc     180

gtagaggtaa agaactatgg tgttaagaat tcagaatgga ttgatgcctg catcaatatt     240

tctcatcatt attgtaatat ttctgatcat gttggtgatc catcaaattc tctttgggtc     300

agagttaaag ccagggttgg acaaaaagaa tctgcctatg caaagtcaga agaatttgct     360

gtatgccgag atggaaaaat tggaccacct aaactggata tcagaaagga ggagaagcaa     420

atcatgattg acatatttca cccttcagtt tttgtaaatg gagacgagca ggaagtcgat     480

tatgatcccg aaactacctg ttacattagg gtgtacaatg tgtatgtgag aatgaacgga     540

agtgagatcc agtataaaat actcacgcag aaggaagatg attgtgacga gattcagtgc     600

cagttagcga ttccagtatc ctcactgaat tctcagtact gtgtttcagc agaaggagtc     660

ttacatgtgt ggggtgttac aactgaaaag tcaaaagaag tttgtattac cattttctcc     720
```

-continued

```
cagctgcccg ctcctcagca cccgaagatt cgcctgtaca acgcagagca ggtcctgagt    780

tgggagccag tggccctgag caatagcacg aggcctgttg tctaccgagt gcagtttaaa    840

tacaccgaca gtaaatggtt cacggccgac atcatgtcca taggggtgaa ttgtacacag    900

atcacagcaa cagagtgtga cttcactgcc gccagtccct cagcaggctt cccaatggat    960

ttcaatgtca ctctacgcct tcgagctgag ctgggagcac tccattctgc ctgggtgaca   1020

atgccttggt ttcaacacta tcggaatgtg actgtcgggc ctccagaaaa cattgaggtg   1080

accccaggag aaggctccct catcatcagg ttctcctctc cctttgacat cgctgatacc   1140

tccacggcct ttttttgtta ttatgtccat tactgggaaa aggaggaat ccaacaggtc   1200

aaaggccctt tcagaagcaa ctccatttca ttggataact taaaaccctc cagagtgtac   1260

tgtttacaag tccaggcaca actgctttgg aacaaaagta acatctttag agtcgggcat   1320

ttaagcaaca tatcttgcta cgaaacaatg gcagatgcct ccactgagct tcaggacaaa   1380

actcacacat gcccaccgtg cccagcacct gaactcctgg ggggaccgtc agtcttcctc   1440

ttccccccaa aacccaagga caccctcatg atctcccgga cccctgaggt cacatgcgtg   1500

gtggtggacg tgagccacga agaccctgag gtcaagttca actggtacgt ggacggcgtg   1560

gaggtgcata atgccaagac aaagccgcgg gaggagcagt acaacagcac gtaccgtgtg   1620

gtcagcgtcc tcaccgtcct gcaccaggac tggctgaatg gcaaggagta caagtgcaag   1680

gtctccaaca aagccctccc agcccccatc gagaaaacca tctccaaagc caaagggcag   1740

ccccgagaac cacaggtgta caccctgccc ccatcccggg atgagctgac caagaaccag   1800

gtcagcctga cctgcctggt caaaggcttc tatcccagcg acatcgccgt ggagtgggag   1860

agcaatgggc agccggagaa caactacaag accacgcctc ccgtgctgga ctccgacggc   1920

tccttcttcc tctacagcaa gctcaccgtg gacaagagca ggtggcagca ggggaacgtc   1980

ttctcatgct ccgtgatgca tgaggctctg cacaaccact acacgcagaa gagcctctcc   2040

ctgtctccgg gtaaa                                                    2055
```

<210> SEQ ID NO 7
<211> LENGTH: 685
<212> TYPE: PRT
<213> ORGANISM: Artificial Sequence
<220> FEATURE:
<223> OTHER INFORMATION: Synthetic

<400> SEQUENCE: 7

```
Met Val Leu Leu Phe Leu Leu Pro Leu Val Met Gln Gly Val Ser Arg
 1               5                  10                  15

Ala Glu Met Gly Thr Ala Asp Leu Gly Pro Ser Ser Val Pro Thr Pro
            20                  25                  30

Thr Asn Val Thr Ile Glu Ser Tyr Asn Met Asn Pro Ile Val Tyr Trp
        35                  40                  45

Glu Tyr Gln Ile Met Pro Gln Val Pro Val Phe Thr Val Glu Val Lys
    50                  55                  60

Asn Tyr Gly Val Lys Asn Ser Glu Trp Ile Asp Ala Cys Ile Asn Ile
65                  70                  75                  80

Ser His His Tyr Cys Asn Ile Ser Asp His Val Gly Asp Pro Ser Asn
                85                  90                  95

Ser Leu Trp Val Arg Val Lys Ala Arg Val Gly Gln Lys Glu Ser Ala
            100                 105                 110

Tyr Ala Lys Ser Glu Glu Phe Ala Val Cys Arg Asp Gly Lys Ile Gly
        115                 120                 125
```

-continued

```
Pro Pro Lys Leu Asp Ile Arg Lys Glu Glu Lys Gln Ile Met Ile Asp
    130                 135                 140

Ile Phe His Pro Ser Val Phe Val Asn Gly Asp Glu Gln Glu Val Asp
145                 150                 155                 160

Tyr Asp Pro Glu Thr Thr Cys Tyr Ile Arg Val Tyr Asn Val Tyr Val
                165                 170                 175

Arg Met Asn Gly Ser Glu Ile Gln Tyr Lys Ile Leu Thr Gln Lys Glu
            180                 185                 190

Asp Asp Cys Asp Glu Ile Gln Cys Gln Leu Ala Ile Pro Val Ser Ser
        195                 200                 205

Leu Asn Ser Gln Tyr Cys Val Ser Ala Glu Gly Val Leu His Val Trp
    210                 215                 220

Gly Val Thr Thr Glu Lys Ser Lys Glu Val Cys Ile Thr Ile Phe Ser
225                 230                 235                 240

Gln Leu Pro Ala Pro Gln His Pro Lys Ile Arg Leu Tyr Asn Ala Glu
                245                 250                 255

Gln Val Leu Ser Trp Glu Pro Val Ala Leu Ser Asn Ser Thr Arg Pro
            260                 265                 270

Val Val Tyr Arg Val Gln Phe Lys Tyr Thr Asp Ser Lys Trp Phe Thr
        275                 280                 285

Ala Asp Ile Met Ser Ile Gly Val Asn Cys Thr Gln Ile Thr Ala Thr
    290                 295                 300

Glu Cys Asp Phe Thr Ala Ala Ser Pro Ser Ala Gly Phe Pro Met Asp
305                 310                 315                 320

Phe Asn Val Thr Leu Arg Leu Arg Ala Glu Leu Gly Ala Leu His Ser
                325                 330                 335

Ala Trp Val Thr Met Pro Trp Phe Gln His Tyr Arg Asn Val Thr Val
            340                 345                 350

Gly Pro Pro Glu Asn Ile Glu Val Thr Pro Gly Glu Gly Ser Leu Ile
        355                 360                 365

Ile Arg Phe Ser Ser Pro Phe Asp Ile Ala Asp Thr Ser Thr Ala Phe
    370                 375                 380

Phe Cys Tyr Tyr Val His Tyr Trp Glu Lys Gly Gly Ile Gln Gln Val
385                 390                 395                 400

Lys Gly Pro Phe Arg Ser Asn Ser Ile Ser Leu Asp Asn Leu Lys Pro
                405                 410                 415

Ser Arg Val Tyr Cys Leu Gln Val Gln Ala Gln Leu Leu Trp Asn Lys
            420                 425                 430

Ser Asn Ile Phe Arg Val Gly His Leu Ser Asn Ile Ser Cys Tyr Glu
        435                 440                 445

Thr Met Ala Asp Ala Ser Thr Glu Leu Gln Asp Lys Thr His Thr Cys
    450                 455                 460

Pro Pro Cys Pro Ala Pro Glu Leu Leu Gly Gly Pro Ser Val Phe Leu
465                 470                 475                 480

Phe Pro Pro Lys Pro Lys Asp Thr Leu Met Ile Ser Arg Thr Pro Glu
                485                 490                 495

Val Thr Cys Val Val Val Asp Val Ser His Glu Asp Pro Glu Val Lys
            500                 505                 510

Phe Asn Trp Tyr Val Asp Gly Val Glu Val His Asn Ala Lys Thr Lys
        515                 520                 525

Pro Arg Glu Glu Gln Tyr Asn Ser Thr Tyr Arg Val Val Ser Val Leu
    530                 535                 540
```

-continued

```
Thr Val Leu His Gln Asp Trp Leu Asn Gly Lys Glu Tyr Lys Cys Lys
545                 550                 555                 560

Val Ser Asn Lys Ala Leu Pro Ala Pro Ile Glu Lys Thr Ile Ser Lys
                565                 570                 575

Ala Lys Gly Gln Pro Arg Glu Pro Gln Val Tyr Thr Leu Pro Pro Ser
            580                 585                 590

Arg Asp Glu Leu Thr Lys Asn Gln Val Ser Leu Thr Cys Leu Val Lys
        595                 600                 605

Gly Phe Tyr Pro Ser Asp Ile Ala Val Glu Trp Glu Ser Asn Gly Gln
    610                 615                 620

Pro Glu Asn Asn Tyr Lys Thr Thr Pro Pro Val Leu Asp Ser Asp Gly
625                 630                 635                 640

Ser Phe Phe Leu Tyr Ser Lys Leu Thr Val Asp Lys Ser Arg Trp Gln
                645                 650                 655

Gln Gly Asn Val Phe Ser Cys Ser Val Met His Glu Ala Leu His Asn
            660                 665                 670

His Tyr Thr Gln Lys Ser Leu Ser Leu Ser Pro Gly Lys
        675                 680                 685
```

```
<210> SEQ ID NO 8
<211> LENGTH: 2055
<212> TYPE: DNA
<213> ORGANISM: Artificial Sequence
<220> FEATURE:
<223> OTHER INFORMATION: Synthetic

<400> SEQUENCE: 8

atggtgctcc tctttctcct accccttgtc atgcagggtg tgagcagggc tgagatgggc     60

accgcggatc tggggccgtc ctcagtgcct acaccaacta atgttacaat tgaatcctat    120

aacatgaacc ctatcgtata ttgggagtac cagatcatgc cacaggtccc tgtttttacc    180

gtagaggtaa agaactatgg tgttaagaat tcagaatgga ttgatgcctg catcaatatt    240

tctcatcatt attgtaatat ttctgatcat gttggtgatc catcaaattc tctttgggtc    300

agagttaaag ccagggttgg acaaaaagaa tctgcctatg caaagtcaga agaatttgct    360

gtatgccgag atggaaaaat tggaccacct aaactggata tcagaaagga ggagaagcaa    420

atcatgattg acatatttca cccttcagtt tttgtaaatg gagacgagca ggaagtcgat    480

tatgatcccg aaactacctg ttacattagg gtgtacaatg tgtatgtgag aatgaacgga    540

agtgagatcc agtataaaat actcacgcag aaggaagatg attgtgacga gattcagtgc    600

cagttagcga ttccagtatc ctcactgaat tctcagtact gtgtttcagc agaaggagtc    660

ttacatgtgt ggggtgttac aactgaaaag tcaaaagaag tttgtattac cattttctcc    720

cagctgcccg ctcctcagca cccgaagatt cgcctgtaca acgcagagca ggtcctgagt    780

tgggagccag tggccctgag caatagcacg aggcctgttg tctaccgagt gcagtttaaa    840

tacaccgaca gtaaatggtt cacggccgac atcatgtcca taggggtgaa ttgtacacag    900

atcacagcaa cagagtgtga cttcactgcc gccagtccct cagcaggctt cccaatggat    960

ttcaatgtca ctctacgcct tcgagctgag ctgggagcac tccattctgc ctgggtgaca   1020

atgccttggt ttcaacacta tcggaatgtg actgtcgggc ctccagaaaa cattgaggtg   1080

accccaggag aaggctccct catcatcagg ttctcctctc cctttgacat cgctgatacc   1140

tccacggcct ttttttcgta ttatgtccat tactgggaaa aaggaggaat ccaacaggtc   1200

aaaggccctt tcagaagcaa ctccatttca ttggataact taaaaccctc cagagtgtac   1260
```

-continued

```
tgtttacaag tccaggcaca actgctttgg aacaaaagta acatctttag agtcgggcat   1320

ttaagcaaca tatcttgcta cgaaacaatg gcagatgcct ccactgagct tcaggacaaa   1380

actcacacat gcccaccgtg cccagcacct gaactcctgg ggggaccgtc agtcttcctc   1440

ttccccccaa aacccaagga caccctcatg atctcccgga cccctgaggt cacatgcgtg   1500

gtggtggacg tgagccacga agaccctgag gtcaagttca actggtacgt ggacggcgtg   1560

gaggtgcata atgccaagac aaagccgcgg gaggagcagt acaacagcac gtaccgtgtg   1620

gtcagcgtcc tcaccgtcct gcaccaggac tggctgaatg gcaaggagta caagtgcaag   1680

gtctccaaca aagccctccc agcccccatc gagaaaacca tctccaaagc caaagggcag   1740

ccccgagaac cacaggtgta caccctgccc ccatcccggg atgagctgac caagaaccag   1800

gtcagcctga cctgcctggt caaaggcttc tatcccagcg acatcgccgt ggagtgggag   1860

agcaatgggc agccggagaa caactacaag accacgcctc ccgtgctgga ctccgacggc   1920

tccttcttcc tctacagcaa gctcaccgtg gacaagagca ggtggcagca ggggaacgtc   1980

ttctcatgct ccgtgatgca tgaggctctg cacaaccact acacgcagaa gagcctctcc   2040

ctgtctccgg gtaaa                                                    2055
```

```
<210> SEQ ID NO 9
<211> LENGTH: 685
<212> TYPE: PRT
<213> ORGANISM: Artificial Sequence
<220> FEATURE:
<223> OTHER INFORMATION: Synthetic

<400> SEQUENCE: 9

Met Val Leu Leu Phe Leu Leu Pro Leu Val Met Gln Gly Val Ser Arg
 1               5                  10                  15

Ala Glu Met Gly Thr Ala Asp Leu Gly Pro Ser Ser Val Pro Thr Pro
            20                  25                  30

Thr Asn Val Thr Ile Glu Ser Tyr Asn Met Asn Pro Ile Val Tyr Trp
        35                  40                  45

Glu Tyr Gln Ile Met Pro Gln Val Pro Val Phe Thr Val Glu Val Lys
    50                  55                  60

Asn Tyr Gly Val Lys Asn Ser Glu Trp Ile Asp Ala Cys Ile Asn Ile
65                  70                  75                  80

Ser His His Tyr Cys Asn Ile Ser Asp His Val Gly Asp Pro Ser Asn
                85                  90                  95

Ser Leu Trp Val Arg Val Lys Ala Arg Val Gly Gln Lys Glu Ser Ala
            100                 105                 110

Tyr Ala Lys Ser Glu Glu Phe Ala Val Cys Arg Asp Gly Lys Ile Gly
        115                 120                 125

Pro Pro Lys Leu Asp Ile Arg Lys Glu Glu Lys Gln Ile Met Ile Asp
    130                 135                 140

Ile Phe His Pro Ser Val Phe Val Asn Gly Asp Glu Gln Glu Val Asp
145                 150                 155                 160

Tyr Asp Pro Glu Thr Thr Cys Tyr Ile Arg Val Tyr Asn Val Tyr Val
                165                 170                 175

Arg Met Asn Gly Ser Glu Ile Gln Tyr Lys Ile Leu Thr Gln Lys Glu
            180                 185                 190

Asp Asp Cys Asp Glu Ile Gln Cys Gln Leu Ala Ile Pro Val Ser Ser
        195                 200                 205

Leu Asn Ser Gln Tyr Cys Val Ser Ala Glu Gly Val Leu His Val Trp
    210                 215                 220
```

-continued

```
Gly Val Thr Thr Glu Lys Ser Lys Glu Val Cys Ile Thr Ile Phe Ser
225                 230                 235                 240

Gln Leu Pro Ala Pro Gln His Pro Lys Ile Arg Leu Tyr Asn Ala Glu
                245                 250                 255

Gln Val Leu Ser Trp Glu Pro Val Ala Leu Ser Asn Ser Thr Arg Pro
            260                 265                 270

Val Val Tyr Arg Val Gln Phe Lys Tyr Thr Asp Ser Lys Trp Phe Thr
        275                 280                 285

Ala Asp Ile Met Ser Ile Gly Val Asn Cys Thr Gln Ile Thr Ala Thr
    290                 295                 300

Glu Cys Asp Phe Thr Ala Ala Ser Pro Ser Ala Gly Phe Pro Met Asp
305                 310                 315                 320

Phe Asn Val Thr Leu Arg Leu Arg Ala Glu Leu Gly Ala Leu His Ser
                325                 330                 335

Ala Trp Val Thr Met Pro Trp Phe Gln His Tyr Arg Asn Val Thr Val
            340                 345                 350

Gly Pro Pro Glu Asn Ile Glu Val Thr Pro Gly Glu Gly Ser Leu Ile
        355                 360                 365

Ile Arg Phe Ser Ser Pro Phe Asp Ile Ala Asp Thr Ser Thr Ala Phe
    370                 375                 380

Phe Ser Tyr Tyr Val His Tyr Trp Glu Lys Gly Gly Ile Gln Gln Val
385                 390                 395                 400

Lys Gly Pro Phe Arg Ser Asn Ser Ile Ser Leu Asp Asn Leu Lys Pro
                405                 410                 415

Ser Arg Val Tyr Cys Leu Gln Val Gln Ala Gln Leu Leu Trp Asn Lys
            420                 425                 430

Ser Asn Ile Phe Arg Val Gly His Leu Ser Asn Ile Ser Cys Tyr Glu
        435                 440                 445

Thr Met Ala Asp Ala Ser Thr Glu Leu Gln Asp Lys Thr His Thr Cys
    450                 455                 460

Pro Pro Cys Pro Ala Pro Glu Leu Leu Gly Gly Pro Ser Val Phe Leu
465                 470                 475                 480

Phe Pro Pro Lys Pro Lys Asp Thr Leu Met Ile Ser Arg Thr Pro Glu
                485                 490                 495

Val Thr Cys Val Val Val Asp Val Ser His Glu Asp Pro Glu Val Lys
            500                 505                 510

Phe Asn Trp Tyr Val Asp Gly Val Glu Val His Asn Ala Lys Thr Lys
        515                 520                 525

Pro Arg Glu Glu Gln Tyr Asn Ser Thr Tyr Arg Val Val Ser Val Leu
    530                 535                 540

Thr Val Leu His Gln Asp Trp Leu Asn Gly Lys Glu Tyr Lys Cys Lys
545                 550                 555                 560

Val Ser Asn Lys Ala Leu Pro Ala Pro Ile Glu Lys Thr Ile Ser Lys
                565                 570                 575

Ala Lys Gly Gln Pro Arg Glu Pro Gln Val Tyr Thr Leu Pro Pro Ser
            580                 585                 590

Arg Asp Glu Leu Thr Lys Asn Gln Val Ser Leu Thr Cys Leu Val Lys
        595                 600                 605

Gly Phe Tyr Pro Ser Asp Ile Ala Val Glu Trp Glu Ser Asn Gly Gln
    610                 615                 620

Pro Glu Asn Asn Tyr Lys Thr Thr Pro Pro Val Leu Asp Ser Asp Gly
625                 630                 635                 640
```

-continued

```
Ser Phe Phe Leu Tyr Ser Lys Leu Thr Val Asp Lys Ser Arg Trp Gln
              645                 650                 655

Gln Gly Asn Val Phe Ser Cys Ser Val Met His Glu Ala Leu His Asn
            660                 665                 670

His Tyr Thr Gln Lys Ser Leu Ser Leu Ser Pro Gly Lys
        675                 680                 685


<210> SEQ ID NO 10
<211> LENGTH: 1398
<212> TYPE: DNA
<213> ORGANISM: Artificial Sequence
<220> FEATURE:
<223> OTHER INFORMATION: Synthetic

<400> SEQUENCE: 10

atggtgctcc tctttctcct accccttgtc atgcagggtg tgagcagggc tgagatgggc      60

accgcggatc tggggccgtc ctcagtgcct acaccaacta atgttacaat tgaatcctat     120

aacatgaacc ctatcgtata ttgggagtac cagatcatgc cacaggtccc tgtttttacc     180

gtagaggtaa agaactatgg tgttaagaat tcagaatgga ttgatgcctg catcaatatt     240

tctcatcatt attgtaatat ttctgatcat gttggtgatc catcaaattc tctttgggtc     300

agagttaaag ccagggttgg acaaaaagaa tctgcctatg caaagtcaga agaatttgct     360

gtatgccgag atggaaaaat tggaccacct aaactggata tcagaaagga ggagaagcaa     420

atcatgattg acatatttca cccttcagtt tttgtaaatg gagacgagca ggaagtcgat     480

tatgatcccg aaactacctg ttacattagg gtgtacaatg tgtatgtgag aatgaacgga     540

agtgagatcc agtataaaat actcacgcag aaggaagatg attgtgacga gattcagtgc     600

cagttagcga ttccagtatc ctcactgaat tctcagtact gtgtttcagc agaaggagtc     660

ttacatgtgt ggggtgttac aactgaaaag tcaaaagaag tttgtattac catttcgac      720

aaaactcaca catgcccacc gtgcccagca cctgaactcc tggggggacc gtcagtcttc     780

ctcttccccc caaaacccaa ggacaccctc atgatctccc ggacccctga ggtcacatgc     840

gtggtggtgg acgtgagcca cgaagaccct gaggtcaagt tcaactggta cgtggacggc     900

gtggaggtgc ataatgccaa gacaaagccg cgggaggagc agtacaacag cacgtaccgt     960

gtggtcagcg tcctcaccgt cctgcaccag gactggctga atggcaagga gtacaagtgc    1020

aaggtctcca acaaagccct cccagccccc atcgagaaaa ccatctccaa agccaaaggg    1080

cagccccgag aaccacaggt gtacaccctg cccccatccc gggatgagct gaccaagaac    1140

caggtcagcc tgacctgcct ggtcaaaggc ttctatccca gcgacatcgc cgtggagtgg    1200

gagagcaatg ggcagccgga gaacaactac aagaccacgc ctcccgtgct ggactccgac    1260

ggctccttct tcctctatag caagctcacc gtggacaaga gcaggtggca gcaggggaac    1320

gtcttctcat gctccgtgat gcatgaggct ctgcacaacc actacacgca gaagagcctc    1380

tccctgtctc cgggtaaa                                                  1398


<210> SEQ ID NO 11
<211> LENGTH: 466
<212> TYPE: PRT
<213> ORGANISM: Artificial Sequence
<220> FEATURE:
<223> OTHER INFORMATION: Synthetic

<400> SEQUENCE: 11

Met Val Leu Leu Phe Leu Leu Pro Leu Val Met Gln Gly Val Ser Arg
 1               5                  10                  15
```

-continued

```
Ala Glu Met Gly Thr Ala Asp Leu Gly Pro Ser Ser Val Pro Thr Pro
            20                  25                  30

Thr Asn Val Thr Ile Glu Ser Tyr Asn Met Asn Pro Ile Val Tyr Trp
        35                  40                  45

Glu Tyr Gln Ile Met Pro Gln Val Pro Val Phe Thr Val Glu Val Lys
    50                  55                  60

Asn Tyr Gly Val Lys Asn Ser Glu Trp Ile Asp Ala Cys Ile Asn Ile
65                  70                  75                  80

Ser His His Tyr Cys Asn Ile Ser Asp His Val Gly Asp Pro Ser Asn
                85                  90                  95

Ser Leu Trp Val Arg Val Lys Ala Arg Val Gly Gln Lys Glu Ser Ala
            100                 105                 110

Tyr Ala Lys Ser Glu Glu Phe Ala Val Cys Arg Asp Gly Lys Ile Gly
        115                 120                 125

Pro Pro Lys Leu Asp Ile Arg Lys Glu Glu Lys Gln Ile Met Ile Asp
    130                 135                 140

Ile Phe His Pro Ser Val Phe Val Asn Gly Asp Glu Gln Glu Val Asp
145                 150                 155                 160

Tyr Asp Pro Glu Thr Thr Cys Tyr Ile Arg Val Tyr Asn Val Tyr Val
                165                 170                 175

Arg Met Asn Gly Ser Glu Ile Gln Tyr Lys Ile Leu Thr Gln Lys Glu
            180                 185                 190

Asp Asp Cys Asp Glu Ile Gln Cys Gln Leu Ala Ile Pro Val Ser Ser
        195                 200                 205

Leu Asn Ser Gln Tyr Cys Val Ser Ala Glu Gly Val Leu His Val Trp
    210                 215                 220

Gly Val Thr Thr Glu Lys Ser Lys Glu Val Cys Ile Thr Ile Phe Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Asp Glu Leu Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430
```

-continued

```
Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465


<210> SEQ ID NO 12
<211> LENGTH: 2067
<212> TYPE: DNA
<213> ORGANISM: Artificial Sequence
<220> FEATURE:
<223> OTHER INFORMATION: Synthetic

<400> SEQUENCE: 12

atggtgctcc tctttctcct accccttgtc atgcagggtg tgagcagggc tgagatgggc     60

accgcggatc tggggccgtc ctcagtgcct acaccaacta atgttacaat tgaatcctat    120

aacatgaacc ctatcgtata ttgggagtac cagatcatgc cacaggtccc tgtttttacc    180

gtagaggtaa agaactatgg tgttaagaat tcagaatgga ttgatgcctg catcaatatt    240

tctcatcatt attgtaatat ttctgatcat gttggtgatc catcaaattc tctttgggtc    300

agagttaaag ccagggttgg acaaaaagaa tctgcctatg caaagtcaga agaatttgct    360

gtatgccgag atggaaaaat tggaccacct aaactggata tcagaaagga ggagaagcaa    420

atcatgattg acatatttca cccttcagtt tttgtaaatg gagacgagca ggaagtcgat    480

tatgatcccg aaactacctg ttacattagg gtgtacaatg tgtatgtgag aatgaacgga    540

agtgagatcc agtataaaat actcacgcag aaggaagatg attgtgacga gattcagtgc    600

cagttagcga ttccagtatc ctcactgaat tctcagtact gtgtttcagc agaaggagtc    660

ttacatgtgt ggggtgttac aactgaaaag tcaaaagaag tttgtattac catttcacc     720

ggatcccagc tgcccgctcc tcagcacccg aagattcgcc tgtacaacgc agagcaggtc    780

ctgagttggg agccagtggc cctgagcaat agcacgaggc ctgttgtcta ccgagtgcag    840

tttaaataca ccgacagtaa atggttcacg gccgacatca tgtccatagg ggtgaattgt    900

acacagatca cagcaacaga gtgtgacttc actgccgcca gtccctcagc aggcttccca    960

atggatttca atgtcactct acgccttcga gctgagctgg gagcactcca ttctgcctgg   1020

gtgacaatgc cttggtttca acactatcgg aatgtgactg tcgggcctcc agaaaacatt   1080

gaggtgaccc caggagaagg ctccctcatc atcaggttct cctctccctt tgacatcgct   1140

gatacctcca cggccttttt ttgttattat gtccattact gggaaaaagg aggaatccaa   1200

caggtcaaag gccctttcag aagcaactcc atttcattgg ataacttaaa accctccaga   1260

gtgtactgtt tacaagtcca ggcacaactg ctttggaaca aaagtaacat ctttagagtc   1320

gggcatttaa gcaacatatc ttgctacgaa acaatggcag atgcctccac tgagcttcag   1380

tccggagaca aaactcacac atgcccaccg tgcccagcac ctgaactcct ggggggaccg   1440

tcagtcttcc tcttcccccc aaaacccaag gacaccctca tgatctcccg gacccctgag   1500

gtcacatgcg tggtggtgga cgtgagccac gaagaccctg aggtcaagtt caactggtac   1560

gtggacggcg tggaggtgca taatgccaag acaaagccgc gggaggagca gtacaacagc   1620

acgtaccgtg tggtcagcgt cctcaccgtc ctgcaccagg actggctgaa tggcaaggag   1680

tacaagtgca aggtctccaa caaagccctc ccagccccca tcgagaaaac catctccaaa   1740

gccaaagggc agccccgaga accacaggtg tacaccctgc ccccatcccg ggatgagctg   1800
```

-continued

```
accaagaacc aggtcagcct gacctgcctg gtcaaaggct tctatcccag cgacatcgcc   1860

gtggagtggg agagcaatgg gcagccggag aacaactaca agaccacgcc tcccgtgctg   1920

gactccgacg gctccttctt cctctacagc aagctcaccg tggacaagag caggtggcag   1980

caggggaacg tcttctcatg ctccgtgatg catgaggctc tgcacaacca ctacacgcag   2040

aagagcctct ccctgtctcc gggtaaa                                       2067


<210> SEQ ID NO 13
<211> LENGTH: 689
<212> TYPE: PRT
<213> ORGANISM: Artificial Sequence
<220> FEATURE:
<223> OTHER INFORMATION: Synthetic

<400> SEQUENCE: 13

Met Val Leu Leu Phe Leu Leu Pro Leu Val Met Gln Gly Val Ser Arg
 1               5                  10                  15

Ala Glu Met Gly Thr Ala Asp Leu Gly Pro Ser Ser Val Pro Thr Pro
            20                  25                  30

Thr Asn Val Thr Ile Glu Ser Tyr Asn Met Asn Pro Ile Val Tyr Trp
        35                  40                  45

Glu Tyr Gln Ile Met Pro Gln Val Pro Val Phe Thr Val Glu Val Lys
    50                  55                  60

Asn Tyr Gly Val Lys Asn Ser Glu Trp Ile Asp Ala Cys Ile Asn Ile
65                  70                  75                  80

Ser His His Tyr Cys Asn Ile Ser Asp His Val Gly Asp Pro Ser Asn
                85                  90                  95

Ser Leu Trp Val Arg Val Lys Ala Arg Val Gly Gln Lys Glu Ser Ala
            100                 105                 110

Tyr Ala Lys Ser Glu Glu Phe Ala Val Cys Arg Asp Gly Lys Ile Gly
        115                 120                 125

Pro Pro Lys Leu Asp Ile Arg Lys Glu Glu Lys Gln Ile Met Ile Asp
    130                 135                 140

Ile Phe His Pro Ser Val Phe Val Asn Gly Asp Glu Gln Glu Val Asp
145                 150                 155                 160

Tyr Asp Pro Glu Thr Thr Cys Tyr Ile Arg Val Tyr Asn Val Tyr Val
                165                 170                 175

Arg Met Asn Gly Ser Glu Ile Gln Tyr Lys Ile Leu Thr Gln Lys Glu
            180                 185                 190

Asp Asp Cys Asp Glu Ile Gln Cys Gln Leu Ala Ile Pro Val Ser Ser
        195                 200                 205

Leu Asn Ser Gln Tyr Cys Val Ser Ala Glu Gly Val Leu His Val Trp
    210                 215                 220

Gly Val Thr Thr Glu Lys Ser Lys Glu Val Cys Ile Thr Ile Phe Thr
225                 230                 235                 240

Gly Ser Gln Leu Pro Ala Pro Gln His Pro Lys Ile Arg Leu Tyr Asn
                245                 250                 255

Ala Glu Gln Val Leu Ser Trp Glu Pro Val Ala Leu Ser Asn Ser Thr
            260                 265                 270

Arg Pro Val Val Tyr Arg Val Gln Phe Lys Tyr Thr Asp Ser Lys Trp
        275                 280                 285

Phe Thr Ala Asp Ile Met Ser Ile Gly Val Asn Cys Thr Gln Ile Thr
    290                 295                 300

Ala Thr Glu Cys Asp Phe Thr Ala Ala Ser Pro Ser Ala Gly Phe Pro
305                 310                 315                 320
```

-continued

```
Met Asp Phe Asn Val Thr Leu Arg Leu Arg Ala Glu Leu Gly Ala Leu
                325                 330                 335

His Ser Ala Trp Val Thr Met Pro Trp Phe Gln His Tyr Arg Asn Val
            340                 345                 350

Thr Val Gly Pro Pro Glu Asn Ile Glu Val Thr Pro Gly Glu Gly Ser
        355                 360                 365

Leu Ile Ile Arg Phe Ser Ser Pro Phe Asp Ile Ala Asp Thr Ser Thr
    370                 375                 380

Ala Phe Phe Cys Tyr Tyr Val His Tyr Trp Glu Lys Gly Gly Ile Gln
385                 390                 395                 400

Gln Val Lys Gly Pro Phe Arg Ser Asn Ser Ile Ser Leu Asp Asn Leu
                405                 410                 415

Lys Pro Ser Arg Val Tyr Cys Leu Gln Val Gln Ala Gln Leu Leu Trp
            420                 425                 430

Asn Lys Ser Asn Ile Phe Arg Val Gly His Leu Ser Asn Ile Ser Cys
        435                 440                 445

Tyr Glu Thr Met Ala Asp Ala Ser Thr Glu Leu Gln Ser Gly Asp Lys
    450                 455                 460

Thr His Thr Cys Pro Pro Cys Pro Ala Pro Glu Leu Leu Gly Gly Pro
465                 470                 475                 480

Ser Val Phe Leu Phe Pro Pro Lys Pro Lys Asp Thr Leu Met Ile Ser
                485                 490                 495

Arg Thr Pro Glu Val Thr Cys Val Val Val Asp Val Ser His Glu Asp
            500                 505                 510

Pro Glu Val Lys Phe Asn Trp Tyr Val Asp Gly Val Glu Val His Asn
        515                 520                 525

Ala Lys Thr Lys Pro Arg Glu Glu Gln Tyr Asn Ser Thr Tyr Arg Val
    530                 535                 540

Val Ser Val Leu Thr Val Leu His Gln Asp Trp Leu Asn Gly Lys Glu
545                 550                 555                 560

Tyr Lys Cys Lys Val Ser Asn Lys Ala Leu Pro Ala Pro Ile Glu Lys
                565                 570                 575

Thr Ile Ser Lys Ala Lys Gly Gln Pro Arg Glu Pro Gln Val Tyr Thr
            580                 585                 590

Leu Pro Pro Ser Arg Asp Glu Leu Thr Lys Asn Gln Val Ser Leu Thr
        595                 600                 605

Cys Leu Val Lys Gly Phe Tyr Pro Ser Asp Ile Ala Val Glu Trp Glu
    610                 615                 620

Ser Asn Gly Gln Pro Glu Asn Asn Tyr Lys Thr Thr Pro Pro Val Leu
625                 630                 635                 640

Asp Ser Asp Gly Ser Phe Phe Leu Tyr Ser Lys Leu Thr Val Asp Lys
                645                 650                 655

Ser Arg Trp Gln Gln Gly Asn Val Phe Ser Cys Ser Val Met His Glu
            660                 665                 670

Ala Leu His Asn His Tyr Thr Gln Lys Ser Leu Ser Leu Ser Pro Gly
        675                 680                 685

Lys
```

<210> SEQ ID NO 14
<211> LENGTH: 2067
<212> TYPE: DNA
<213> ORGANISM: Artificial Sequence
<220> FEATURE:
<223> OTHER INFORMATION: Synthetic -continued

<400> SEQUENCE: 14
atggtgctcc tctttctcct accccttgtc atgcagggtg tgagcagggc tgagatgggc 60
accgcggatc tggggccgtc ctcagtgcct acaccaacta atgttacaat tgaatcctat 120
aacatgaacc ctatcgtata ttgggagtac cagatcatgc cacaggtccc tgtttttacc 180
gtagaggtaa agaactatgg tgttaagaat tcagaatgga ttgatgcctg catcaatatt 240
tctcatcatt attgtaatat ttctgatcat gttggtgatc catcaaattc tctttgggtc 300
agagttaaag ccagggttgg acaaaaagaa tctgcctatg caaagtcaga agaatttgct 360
gtatgccgag atggaaaaat tggaccacct aaactggata tcagaaagga ggagaagcaa 420
atcatgattg acatatttca cccttcagtt tttgtaaatg gagacgagca ggaagtcgat 480
tatgatcccg aaactacctg ttacattagg gtgtacaatg tgtatgtgag aatgaacgga 540
agtgagatcc agtataaaat actcacgcag aaggaagatg attgtgacga gattcagtgc 600
cagttagcga ttccagtatc ctcactgaat tctcagtact gtgtttcagc agaaggagtc 660
ttacatgtgt ggggtgttac aactgaaaag tcaaaagaag tttgtattac cattttcacc 720
ggatcccagc tgcccgctcc tcagcacccg aagattcgcc tgtacaacgc agagcaggtc 780
ctgagttggg agccagtggc cctgagcaat agcacgaggc ctgttgtcta ccgagtgcag 840
tttaaataca ccgacagtaa atggttcacg gccgacatca tgtccatagg ggtgaattgt 900
acacagatca cagcaacaga gtgtgacttc actgccgcca gtccctcagc aggcttccca 960
atggatttca atgtcactct acgccttcga gctgagctgg gagcactcca ttctgcctgg 1020
gtgacaatgc cttggtttca acactatcgg aatgtgactg tcgggcctcc agaaaacatt 1080
gaggtgaccc caggagaagg ctccctcatc atcaggttct cctctccctt tgacatcgct 1140
gatacctcca cggccttttt ttcgtattat gtccattact gggaaaaagg aggaatccaa 1200
caggtcaaag gccctttcag aagcaactcc atttcattgg ataacttaaa accctccaga 1260
gtgtactgtt tacaagtcca ggcacaactg ctttggaaca aaagtaacat ctttagagtc 1320
gggcatttaa gcaacatatc ttgctacgaa acaatggcag atgcctccac tgagcttcag 1380
tccggagaca aaactcacac atgcccaccg tgcccagcac ctgaactcct ggggggaccg 1440
tcagtcttcc tcttcccccc aaaacccaag gacaccctca tgatctcccg gacccctgag 1500
gtcacatgcg tggtggtgga cgtgagccac gaagaccctg aggtcaagtt caactggtac 1560
gtggacggcg tggaggtgca taatgccaag acaaagccgc gggaggagca gtacaacagc 1620
acgtaccgtg tggtcagcgt cctcaccgtc ctgcaccagg actggctgaa tggcaaggag 1680
tacaagtgca aggtctccaa caaagccctc ccagccccca tcgagaaaac catctccaaa 1740
gccaaagggc agccccgaga accacaggtg tacaccctgc ccccatcccg ggatgagctg 1800
accaagaacc aggtcagcct gacctgcctg gtcaaaggct tctatcccag cgacatcgcc 1860
gtggagtggg agagcaatgg gcagccggag aacaactaca agaccacgcc tcccgtgctg 1920
gactccgacg gctccttctt cctctacagc aagctcaccg tggacaagag caggtggcag 1980
caggggaacg tcttctcatg ctccgtgatg catgaggctc tgcacaacca ctacacgcag 2040
aagagcctct ccctgtctcc gggtaaa 2067

<210> SEQ ID NO 15
<211> LENGTH: 689
<212> TYPE: PRT
<213> ORGANISM: Artificial Sequence
<220> FEATURE:

-continued

<223> OTHER INFORMATION: Synthetic

<400> SEQUENCE: 15

```
Met Val Leu Leu Phe Leu Leu Pro Leu Val Met Gln Gly Val Ser Arg
 1               5                  10                  15

Ala Glu Met Gly Thr Ala Asp Leu Gly Pro Ser Ser Val Pro Thr Pro
            20                  25                  30

Thr Asn Val Thr Ile Glu Ser Tyr Asn Met Asn Pro Ile Val Tyr Trp
        35                  40                  45

Glu Tyr Gln Ile Met Pro Gln Val Pro Val Phe Thr Val Glu Val Lys
    50                  55                  60

Asn Tyr Gly Val Lys Asn Ser Glu Trp Ile Asp Ala Cys Ile Asn Ile
65                  70                  75                  80

Ser His His Tyr Cys Asn Ile Ser Asp His Val Gly Asp Pro Ser Asn
                85                  90                  95

Ser Leu Trp Val Arg Val Lys Ala Arg Val Gly Gln Lys Glu Ser Ala
            100                 105                 110

Tyr Ala Lys Ser Glu Glu Phe Ala Val Cys Arg Asp Gly Lys Ile Gly
        115                 120                 125

Pro Pro Lys Leu Asp Ile Arg Lys Glu Glu Lys Gln Ile Met Ile Asp
    130                 135                 140

Ile Phe His Pro Ser Val Phe Val Asn Gly Asp Glu Gln Glu Val Asp
145                 150                 155                 160

Tyr Asp Pro Glu Thr Thr Cys Tyr Ile Arg Val Tyr Asn Val Tyr Val
                165                 170                 175

Arg Met Asn Gly Ser Glu Ile Gln Tyr Lys Ile Leu Thr Gln Lys Glu
            180                 185                 190

Asp Asp Cys Asp Glu Ile Gln Cys Gln Leu Ala Ile Pro Val Ser Ser
        195                 200                 205

Leu Asn Ser Gln Tyr Cys Val Ser Ala Glu Gly Val Leu His Val Trp
    210                 215                 220

Gly Val Thr Thr Glu Lys Ser Lys Glu Val Cys Ile Thr Ile Phe Thr
225                 230                 235                 240

Gly Ser Gln Leu Pro Ala Pro Gln His Pro Lys Ile Arg Leu Tyr Asn
                245                 250                 255

Ala Glu Gln Val Leu Ser Trp Glu Pro Val Ala Leu Ser Asn Ser Thr
            260                 265                 270

Arg Pro Val Val Tyr Arg Val Gln Phe Lys Tyr Thr Asp Ser Lys Trp
        275                 280                 285

Phe Thr Ala Asp Ile Met Ser Ile Gly Val Asn Cys Thr Gln Ile Thr
    290                 295                 300

Ala Thr Glu Cys Asp Phe Thr Ala Ala Ser Pro Ser Ala Gly Phe Pro
305                 310                 315                 320

Met Asp Phe Asn Val Thr Leu Arg Leu Arg Ala Glu Leu Gly Ala Leu
                325                 330                 335

His Ser Ala Trp Val Thr Met Pro Trp Phe Gln His Tyr Arg Asn Val
            340                 345                 350

Thr Val Gly Pro Pro Glu Asn Ile Glu Val Thr Pro Gly Glu Gly Ser
        355                 360                 365

Leu Ile Ile Arg Phe Ser Ser Pro Phe Asp Ile Ala Asp Thr Ser Thr
    370                 375                 380

Ala Phe Phe Ser Tyr Tyr Val His Tyr Trp Glu Lys Gly Gly Ile Gln
385                 390                 395                 400
```

-continued

```
Gln Val Lys Gly Pro Phe Arg Ser Asn Ser Ile Ser Leu Asp Asn Leu
                405                 410                 415

Lys Pro Ser Arg Val Tyr Cys Leu Gln Val Gln Ala Gln Leu Leu Trp
            420                 425                 430

Asn Lys Ser Asn Ile Phe Arg Val Gly His Leu Ser Asn Ile Ser Cys
        435                 440                 445

Tyr Glu Thr Met Ala Asp Ala Ser Thr Glu Leu Gln Ser Gly Asp Lys
    450                 455                 460

Thr His Thr Cys Pro Pro Cys Pro Ala Pro Glu Leu Leu Gly Gly Pro
465                 470                 475                 480

Ser Val Phe Leu Phe Pro Pro Lys Pro Lys Asp Thr Leu Met Ile Ser
                485                 490                 495

Arg Thr Pro Glu Val Thr Cys Val Val Val Asp Val Ser His Glu Asp
            500                 505                 510

Pro Glu Val Lys Phe Asn Trp Tyr Val Asp Gly Val Glu Val His Asn
        515                 520                 525

Ala Lys Thr Lys Pro Arg Glu Glu Gln Tyr Asn Ser Thr Tyr Arg Val
    530                 535                 540

Val Ser Val Leu Thr Val Leu His Gln Asp Trp Leu Asn Gly Lys Glu
545                 550                 555                 560

Tyr Lys Cys Lys Val Ser Asn Lys Ala Leu Pro Ala Pro Ile Glu Lys
                565                 570                 575

Thr Ile Ser Lys Ala Lys Gly Gln Pro Arg Glu Pro Gln Val Tyr Thr
            580                 585                 590

Leu Pro Pro Ser Arg Asp Glu Leu Thr Lys Asn Gln Val Ser Leu Thr
        595                 600                 605

Cys Leu Val Lys Gly Phe Tyr Pro Ser Asp Ile Ala Val Glu Trp Glu
    610                 615                 620

Ser Asn Gly Gln Pro Glu Asn Asn Tyr Lys Thr Thr Pro Pro Val Leu
625                 630                 635                 640

Asp Ser Asp Gly Ser Phe Phe Leu Tyr Ser Lys Leu Thr Val Asp Lys
                645                 650                 655

Ser Arg Trp Gln Gln Gly Asn Val Phe Ser Cys Ser Val Met His Glu
            660                 665                 670

Ala Leu His Asn His Tyr Thr Gln Lys Ser Leu Ser Leu Ser Pro Gly
        675                 680                 685

Lys
```

INTERFERON-γ ANTAGONISTS AND THERAPEUTIC USES THEREOF

CROSS-REFERENCE TO RELATED APPLICATIONS

This application claims the benefit under 35 USC § 119(e) of U.S. Provisional 60/697,689 filed 8 Jul. 2005, which application is herein specifically incorporated by reference in its entirety.

BACKGROUND OF THE INVENTION

1. Field of the Invention

The invention encompasses fusion proteins and multimers capable of binding and inhibiting human interferon gamma (IFNγ), as well as therapeutic uses of such polypeptides.

2. Description of Related Art

Interferon gamma (IFNγ) is a lymphokine produced by activated T-lymphocytes. It is known as an immune stimulant because of its ability to activate monocytes and macrophages towards cell killing in vitro (Lee et al. (1983) J Immunol 131:221-2823). U.S. Pat. No. 4,897,264 describes three different types of human IFNγ receptors having molecular weights 90-105 KDa, 140 KDa, and 95-115 KDa. EP 393 502 provides the full-length human IFNγRα sequence of 489 amino acids (SEQ ID NO:1-2) (also known as CD119). U.S. Pat. No. 5,221,789 describes a fragment of human IFNγ receptor alpha (IFNγRα) from position 54-70. Soluble IFNγRα proteins (EP 393 502) and chimeric fusion proteins having a fragment of an IFNγRα receptor fused to an immunoglobulin component (EP 614 981) have been described. WO 95/16036 describes human IFNγ receptor beta (IFNγRβ) having 337 amino acids (SEQ ID NO:3-4) (also known as AF-1).

BRIEF SUMMARY OF THE INVENTION

In a first aspect, the invention features a nucleic acid molecule encoding an interferon γ-binding fusion protein $(R1)_x$–$(R2)_y$–F, wherein R1 comprises a fragment of the extracellular domain of interferon gamma receptor alpha (IFNγRα) component, optionally modified, R2 comprises the extracellular domain of interferon gamma receptor beta (IFNγRβ) component or a fragment or modified fragment thereof, F is a fusion component, and x and y are each independently a positive integer $\geqq 1$, for example between 1 and 10, preferably x and y are each independently 1. The wild-type human IFNγRα and IFNγRβ nucleic acid and amino acid sequences are shown in SEQ ID NO:1-2 and SEQ ID NO:3-4, respectively.

In one embodiment, R1 is amino acids 1-239 of SEQ ID NO:2 (includes a signal peptide at positions 1-17), optionally modified with one or more amino acid substitutions, and R2 is amino acids 28-246 of SEQ ID NO:4, optionally modified with one or more amino acid substitutions. Optionally, $(R1)_x$–$(R2)_y$–F further comprises a signal sequence (SS).

The optional fusion component (F) comprises any component that enhances the functionality of the fusion polypeptide. Thus, for example, a fusion component may enhance the biological activity of the fusion polypeptide, aid in its production and/or recovery, or enhance a pharmacological property or the pharmacokinetic profile of the fusion polypeptide by, for example, enhancing its serum half-life, tissue penetrability, lack of immunogenicity, or stability. In preferred embodiments, the fusion component is selected from the group consisting of a multimerizing component, a serum protein, or a molecule capable of binding a serum protein.

When the fusion component is a multimerizing component, the fusion component includes any natural or synthetic sequence capable of interacting with any other multimerizing component to form a higher order structure, e.g., a dimer, a trimer, etc. In specific embodiments, the multimerizing component is selected from the group consisting of (i) an immunoglobulin-derived domain, (ii) an amino acid sequence between 1 to about 500 amino acids in length, optionally comprising at least one cysteine residue, (iii) a leucine zipper, (iv) a helix loop motif, and (v) a coil-coil motif. In a specific embodiment, the immunoglobulin-derived domain is selected from the group consisting of the Fc domain of IgG or the heavy chain of IgG. In another specific embodiment, the Fc domain of IgG is human FcΔ1 (a), an Fc molecule comprising a mutation of the region involved in forming the disulfide bond with the light chain.

When the fusion component is a serum protein, the serum protein may be any serum protein or a fragment of a serum protein. When the fusion component is a molecule capable of binding a serum protein, it may be a small molecule, a nucleic acid, a peptide, or an oligosaccharide. The fusion component may also be a protein such as FcγR1, ScFv, etc. In preferred embodiments, the fusion component is encoded by the nucleic acid that encodes the fusion polypeptide of the invention. In some embodiments, however, such as when the fusion component is an oligosaccharide, the fusion component is attached post-translationally to the expressed fusion polypeptide.

The nucleic acid molecule of the invention may further optionally comprise a signal sequence (SS) component. When a SS is part of the polypeptide, any SS known to the art may be used, including synthetic or natural sequences from any source, for example, from a secreted or membrane bound protein. In a preferred embodiment, an ROR signal sequence is used (SEQ ID NO:5).

In specific embodiments, the invention features a nucleic acid molecule encoding the fusion polypeptide hIFNγRα. hIFNγRβ.hFc (SEQ ID NO:7) or hIFNγRα.hIFNγRβ (C174S).hFc (SEQ ID NO:9). In a more specific embodiment, the nucleic acid molecule is SEQ ID NO:6 or SEQ ID NO:8.

In a related second aspect, the invention features a vector comprising a nucleic acid molecule of the invention. In third and fourth aspects, the invention encompasses expression vectors comprising the nucleic acid molecules operatively linked to an expression control sequence, and host-vector systems for the production of a fusion polypeptide that comprise the expression vector, in a suitable host cell; host-vector systems, wherein the suitable host cell is, without limitation, a bacterial, yeast, insect, mammalian or plant cell, such as tobacco; or animals such as cows, mice, or rabbits. Examples of suitable cells include *E. coli, B. subtilis*, BHK, COS and CHO cells. Fusion polypeptides modified by acetylation or pegylation are also encompassed by the invention.

In a fifth aspect, the invention features a method of producing a fusion polypeptide of the invention, comprising culturing a host cell transfected with a vector comprising a nucleic acid molecule of the invention, under conditions suitable for expression of the protein from the host cell, and recovering the polypeptide so produced.

In a sixth aspect, the invention features a fusion polypeptide comprising from N- to C-terminus, $(R1)_x$-$(R2)_y$-F, wherein R1, R2, F, x and y are as described above. X and y are preferably each a number between 1-10; preferably x and y are each 1. In specific embodiments, the fusion polypeptide is an amino acid sequence selected from the group consisting of SEQ ID NO:7 and 9. In particular embodiments, the cysteine residue at position 174 of IFNγRβ may be mutated to another amino acid, such as for example, serine, to eliminate disulfide bond scrambling of the protein and improving the production quality of the protein. In specific embodiments, Cys174 is mutated to Ser, Ala, Val, or Met.

In a seventh aspect, the invention features a multimeric protein, comprising two or more fusion polypeptides of the invention. In a specific embodiment, the multimeric protein is a dimer. The interferon γ-binding multimers of the invention are capable of binding interferon γ with an affinity of at least $10^{-8}$ M, preferably at least $10^{-9}$ M, even more preferably at least $10^{-10}$ M, as determined by assay methods known in the art. Generally, the ability of the dimeric interferon γ-binding protein to inhibit (e.g., block) the biological activity of interferon γ, may be measured by bioassay. Bioassays may include luciferase-based assays using an ISRE or GAS promoter element, interferon γ stimulation of cell lines such as HT29 to produce IP-10 and/or interferon γ stimulation of peripheral blood lymphocytes to increase cell surface expression of MHC class II molecules.

In an eighth aspect, the invention features pharmaceutical compositions comprising a fusion polypeptide of the invention with a pharmaceutically acceptable carrier. Such pharmaceutical compositions may comprise a monomeric or multimeric polypeptide, or nucleic acids encoding the fusion polypeptide.

The interferon γ-binding multimers of the invention are therapeutically useful for treating any disease or condition which is improved, ameliorated, or inhibited by removal, inhibition, or reduction of interferon γ. In a ninth aspect, the invention features a method comprising administering to a patient having or at risk of developing a disease or condition which is ameliorated, inhibited, or treated with an inhibitor of interferon γ (IFNγ) a therapeutically or preventatively effect amount of a pharmaceutical composition of the invention. In one embodiment, the condition treated is inflammatory bowel disease, such as ulcerative colitis or Crohn's disease. In another embodiment, the disease or condition is insulin-dependent diabetes, systemic lupus erythematosus, thyroiditis, multiple sclerosis, fulminant hepatitis, allograft rejection, thrombosis and hemorrhage following generalized Shwartzman-type reaction, and Kawasaki disease (mucocutaneous lymph node syndrome), AIDS, rheumatoid arthritis, including juvenile rheumatoid arthritis, Addison's disease, diabetes (type I), epididymitis, glomerulonephritis, Graves' disease, Guillain-Barre syndrome, Hashimoto's disease, hemolytic anemia, lupus nephritis, myasthenia gravis, pemphigus, psoriasis, psoriatic arthritis, atherosclerosis, erythropoietin resistance, graft versus host disease, transplant rejection, autoimmune hepatitis-induced hepatic injury, biliary cirrhosis, alcohol-induced liver injury including alcoholic cirrhosis, rheumatic fever, sarcoidosis, scleroderma, Sjogren's syndrome, spondyloarthropathies including ankylosing spondylitis, or vasculitis. Although any mammal can be treated by the therapeutic methods of the invention, the subject is preferably a human patient suffering from or at risk of suffering from a condition or disease which can be improved, ameliorated, inhibited or treated with a fusion polypeptide of the invention.

In a further aspect, the invention further features diagnostic and prognostic methods, as well as kits for detecting, quantifying, and/or monitoring interferon y with the fusion polypeptides of the invention.

Other objects and advantages will become apparent from a review of the ensuing detailed description.

DETAILED DESCRIPTION OF THE INVENTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to describe the methods and/or materials in connection with which the publications are cited.

Definitions

The term "affinity for" interferon y means that the multimeric fusion proteins of the invention binds the intended cytokine(s) with an affinity of at least $10^{-8}$ M, preferably at least $10^{-9}$ M, even more preferably at least $10^{-10}$ M as determined by assay methods known in the art, for example, surface plasmon resonance (BiaCore ™) analysis. The multimeric fusion polypeptide of the invention is capable of specifically binding to interferon γ, with an affinity (Kd) of at least about $10^{-9}$ M, or preferably at least about $1.3 \times 10^{-11}$ M, as determined surface plasmon resonance.

The term "capable of specifically blocking interferon γ" means the interferon γ-binding fusion polypeptides of the invention form multimers that inhibit the biological activity of the target cytokines, as measured by bioassay. Bioassays may include luciferase-based assays using an ISRE or GAS promoter element, and/or interferon γ stimulation of cell lines such as HT29. "IC50" is defined as the concentration of fusion protein required to inhibit 50% of the response to interferon γ as measured in a bioassay. In a bioassay, such as the ISRE-luciferase assay described below, the interferon γ-specific multimeric proteins of the invention exhibit an IC50 of at least $1 \times 10^{-8}$ M, more preferably at least $1 \times 10^{-9}$ M, and most preferably with an IC50 of at least $1 \times 10^{-10}$ M.

The terms "treatment", "treating", and the like are used herein to generally include obtaining a desired pharmacologic and/or physiologic effect. The effect may be prophylactic in terms of completely or partially preventing a disease, condition, or symptoms thereof, and/or may be therapeutic in terms of a partial or complete cure for a disease or condition and/or adverse effect attributable to the disease or condition. "Treatment" as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition, i.e., arresting its development; or (c) relieving the disease or condition, i.e., causing regression of the disease or condition. The population of subjects treated by the method of the invention includes subjects suffering from the undesirable condition or disease, as well as subjects at risk for development of the condition or disease.

By the term "therapeutically effective dose" is meant a dose that produces the desired effect for which it is administered. The exact dose will depend on the purpose of the treatment, and will be ascertainable by one skilled in the art using known techniques (see, for example, Lloyd (1999) The Art, Science and Technology of Pharmaceutical Compounding).

As used herein, a "condition or disease" generally encompasses a condition of a mammalian host, particularly a human host, which is undesirable and/or injurious to the host. Thus, treating a condition or disorder with an interferon γ-binding fusion polypeptide will encompass the treatment of a mammal, in particular, a human, who has symptoms reflective of elevated or deleterious interferon γ, or who is expected to have such decreased activation in response to a disease, condition or treatment regimen. Treating an interferon γ-related condition or disease encompasses the treatment of a human subject wherein reducing interferon y levels with the fusion polypeptide of the invention results in amelioration of an undesirable symptom resulting from the interferon γ-related condition or disease.

"Inflammatory bowel disease (IBD)" includes conditions such as ulcerative colitis (UC) and Crohn's disease (CD). Although UC and CD and generally considered different diseases, they are both characterized by patchy necrosis of the surface epithelium, focal accumulations of leukocytes adjacent to glandular crypts, and an increased number of intraepithelial lymphocytes (IEL), and thus may be treated as a single disease group.

General Description

Interferon gamma (IFNγ), also known as immune interferon, is a member of the interferon family, which exhibits the antiviral and anti-proliferative properties characteristic of interferons-α, and -β but, in contrast to those interferons, is pH 2 labile. Human IFNγ includes a family of related polypeptide molecules that comprise the full-length human IFNγ (Gray et al. (1982) Nature 295:503-508), a variant lacking the first three N-terminal amino acids, and other amino acid sequence variants.

IFNγ receptors have been purified from different human cells (Aguet et al. (1987) J. Exp. Med. 165:988-999; Novick et al. (1987) J. Biol. Chem. 262:8483-8487; Calderon et al. (1988) Proc. Natl. Acad. Sci. USA 85:4837-4841), including IFNγ receptor a (EP 614 981 A1) and IFNγ receptor β (WO 95/16036).

Nucleic Acid Constructs and Expression

The present invention provides for the construction of nucleic acid molecules encoding interferon γ-binding polypeptides. As described above, the nucleic acid molecules of the invention encode modified fragments of the wild-type (or naturally occurring) human IFNγRα and/or IFNγRβ proteins. Accordingly, the nucleic acid molecules may be termed "recombinant", "artificial", or "synthetic" as they are not nucleic acid molecules found in nature, e.g., not naturally occurring sequences, but are sequences constructed by recombinant DNA technology.

These nucleic acid molecules are inserted into a vector that is able to express the fusion polypeptides of the invention when introduced into an appropriate host cell. Appropriate host cells include, but are not limited to, bacterial, yeast, insect, and mammalian cells. Any of the methods known to one skilled in the art for the insertion of DNA fragments into a vector may be used to construct expression vectors encoding the fusion polypeptides of the invention under control of transcriptional and/or translational control signals.

Expression of the nucleic acid molecules of the invention may be regulated by a second nucleic acid sequence so that the molecule is expressed in a host transformed with the recombinant DNA molecule. For example, expression may be controlled by any promoter/enhancer element known in the art. Promoters which may be used to control expression of the chimeric polypeptide molecules may include any promoter known in the art.

Expression vectors capable of being replicated in a bacterial or eukaryotic host comprising the nucleic acid molecules of the invention are used to transfect the host and thereby direct expression of such nucleic acids to produce the fusion polypeptides of the invention. Transfected cells may transiently or, preferably, constitutively and permanently express the polypeptides of the invention. When the polypeptide so expressed comprises a fusion component such as a multimerizing component capable of associating with a multimerizing component of a second polypeptide, the monomers thus expressed multimerize due to the interactions between the multimerizing components to form a multimeric polypeptide (WO 00/18932, herein specifically incorporated by reference).

R1 and R2 Components

Interferon γ binds to a common receptor composed of two subunits (IFNγRα and IFNγRβ). Naturally occurring wild-type IFNγRα protein is a 489-amino acid protein having the amino acid sequence of SEQ ID NO:2. R1 is an IFNγRα-derived component having amino acids 1-239 SEQ ID NO:2, or a modified fragment thereof. Naturally occurring human wild-type IFNγRβ protein is a 337-amino acid protein having the amino acid sequence shown in SEQ ID NO:4. R2 is an IFNγRβ fragment having amino acids 28-246 of SEQ ID NO:4, or a variant thereof. Optionally, either or both components can be further modified to provide fusion proteins with specifically desired properties, such as, for example, improved solubility, reduced immunogenicity, improved PK, improved production characteristics, and/or improved ability to block interferon γ activity. One of skill in the art may determine what types of modifications may be made to improve or confer a desired characteristic, for example, see PCT/US05/006266, herein specifically incorporated by reference.

Fusion Components

The fusion proteins of the invention comprise a fusion component (F) that, in specific embodiments, is selected from the group consisting of a multimerizing component, a serum protein, or a molecule capable of binding a serum protein. When F comprises a multimerizing component, it includes any natural or synthetic sequence capable of interacting with another multimerizing component to form a higher order structure, e.g., a dimer, a trimer, etc. The multimerizing component may be selected from the group consisting of (i) a multimerizing component, (ii) a truncated multimerizing component, (iii) an amino acid sequence between 1 to about 500 amino acids in length, (iv) a leucine zipper, (v) a helix loop motif, and (vi) a coil-coil motif. When F is a multimerizing component comprising an amino acid sequence between 1 to about 500 amino acids in length, the sequence may contain one or more cysteine residues capable of forming a disulfide bond with a corresponding cysteine residue on another fusion polypeptide comprising an F with one or more cysteine residues.

In a preferred embodiment, the multimerizing component comprises one or more immunoglobulin-derived domains from human IgG, IgM or IgA. In specific embodiments, the immunoglobulin-derived domain is selected from the group consisting of the Fc domain of IgG or the heavy chain of IgG. The Fc domain of IgG may be selected from the isotypes IgG1, IgG2, IgG3, and IgG4, as well as any allotype within each isotype group. In a specific embodiment, F is the Fc domain of IgG4 with Ser228 (Kabat numbering) mutated to Pro to stabilize covalent dimer formation (Mol. Immunol. (1993) 30:105-108) and/or Leu235→Glu which eliminates residual effector functions (Reddy et al. (2000) J. Immunol. 164:1925-1933). In a preferred embodiment, F is the Fc domain of IgG1, or a derivative thereof which may be modified for specifically desired properties (see, for example, Armour et al. (2003) Mol. Immunol. 40:585-593; Shields et al. (2001) J. Biol. Chem. 276:6591-6604). In specific embodiments, the fusion polypeptide of the invention comprises one or two Fc domain(s) of IgG1. In one embodiment, F is an Fc derived from IgG2 or IgG4.

In one embodiment, F is a serum protein or fragment thereof and is selected from the group consisting of α-1-microglobulin, AGP-1, orosomuciod, α-1-acid glycoprotein, vitamin D binding protein (DBP), hemopexin, human serum albumin (hSA), transferrin, ferritin, afamin, haptoglobin, α-fetoprotein thyroglobulin, α-2-HS-glycoprotein, β-2-glycoprotein, hyaluronan-binding protein, syntaxin, C1R, C1q a chain, galectin3-Mac2 binding protein, fibrinogen, polymeric Ig receptor (PIGR), α-2-macroglobulin, urea transport protein, haptoglobin, IGFBPs, macrophage scavenger receptors, fibronectin, giantin, Fc, α-1-antichyromotrypsin, α-1-antitrypsin, antithrombin III, apolipoprotein A-l, apolipoprotein B, β-2-microglobulin, ceruloplasmin, complement component C3 or C4, Cl esterase inhibitor, C-reactive protein, cystatin C, and protein C. In a specific embodiment, F is selected from the group consisting of α-1-microglobulin, AGP-1, orosomuciod, α-1-acid glycoprotein, vitamin D binding protein (DBP), hemopexin, human serum albumin (hSA), afamin, and haptoglobin. The inclusion of an F component may extend the serum half-life of the interferon α/β-binding polypeptide of the invention when desired. See, for example, U.S. Pat. Nos. 6,423,512, 5,876,969, 6,593,295, and 6,548, 653, herein specifically incorporated by reference in their entirety, for examples of serum albumin fusion proteins.

When F is a molecule capable of binding a serum protein, the molecule may be a synthetic small molecule, a lipid or liposome, a nucleic acid, including a synthetic nucleic acid such as an aptomer, a peptide, or an oligosaccharide. The molecule may further be a protein, such as, for example, FcγR1, FcγR2, FcγR3, polymeric Ig receptor (PIGR), ScFv, and other antibody fragments specific for a serum protein.

Optional Spacers

Components of the fusion proteins of the invention may be connected directly to each other or be connected via spacers. Generally, the term "spacer" (or linker) means one or more molecules, e.g., nucleic acids or amino acids, or non-peptide moieties, such as polyethylene glycol, which may be inserted between one or more component domains. For example, spacer sequences may be used to provide a desirable site of interest between components for ease of manipulation. A spacer may also be provided to enhance expression of the fusion protein from a host cell, to decrease steric hindrance such that the component may assume its optimal tertiary structure and/or interact appropriately with its target molecule. For spacers and methods of identifying desirable spacers, see, for example, George et al. (2003) Protein Engineering 15:871-879, herein specifically incorporated by reference. A spacer sequence may include one or more amino acids naturally connected to a receptor component, or may be an added sequence used to enhance expression of the fusion protein, provide specifically desired sites of interest, allow component domains to form optimal tertiary structures and/or to enhance the interaction of a component with its target molecule. In one embodiment, the spacer comprises one or more peptide sequences between one or more components that are between 1-100 amino acids, preferably 1-25. In a specific embodiment, the spacer is a two amino acid sequence, for example SG, RS, TG, etc.

Inhibition of Interferon γ Biological Activity

The fusion proteins of the invention are capable of inhibiting the biological activity of interferon γ with an IC50 (concentration of fusion protein required to inhibit 50% of the response to interferon γ) of at least $1\times10^{-8}$ M, more preferably $1\times10^{-9}$ M and most preferably $1\times10^{-10}$ M in a luciferase assay. Other bioassays useful to determine IC50 are known to the art, including, for example, IFNγ stimulation of peripheral blood lymphocytes and/or HT29 cells.

Therapeutic Uses

The fusion polypeptides of the invention are therapeutically useful for treating any disease or condition which is improved, ameliorated, inhibited or prevented by removal, inhibition, or reduction of interferon γ. Interferon γ has been implicated in a variety of clinical conditions, such as inflammatory bowel disease (IBD), such as ulcerative colitis or Crohn's disease, insulin-dependent diabetes, systemic lupus erythematosus, thyroiditis, multiple sclerosis, fulminant hepatitis, allograft rejection, thrombosis and hemorrhage following generalized Shwartzman-type reaction, Kawasaki disease (mucocutaneous lymph node syndrome), AIDS, rheumatoid arthritis, including juvenile rheumatoid arthritis, Addison's disease, diabetes (type I), epididymitis, glomerulonephritis, Graves' disease, Guillain-Barre syndrome, Hashimoto's disease, hemolytic anemia, lupus nephritis, myasthenia gravis, pemphigus, psoriasis, psoriatic arthritis, atherosclerosis, erythropoietin resistance, graft versus host disease, transplant rejection, autoimmune hepatitis-induced hepatic injury, biliary cirrhosis, alcohol-induced liver injury including alcoholic cirrhosis, rheumatic fever, sarcoidosis, scleroderma, Sjogren's syndrome, spondyloarthropathies including ankylosing spondylitis, or vasculitis. Although any mammal can be treated by the therapeutic methods of the invention, the subject is preferably a human patient suffering from or at risk of suffering from a condition or disease which can be improved, ameliorated, inhibited or treated with a fusion polypeptide of the invention.

Combination Therapies

In numerous embodiments, the fusion polypeptides of the invention may be administered in combination with one or more additional compounds or therapies. For example, multiple fusion polypeptides can be co-administered, or one polypeptide can be administered in conjunction with one or more therapeutic compounds. A benefit of the combined use of the fusion polypeptide of the invention with a second therapeutic agent is that combined use can provide improved efficacy and/or reduced toxicity of either therapeutic agent.

Methods of Administration

The invention provides methods of treatment comprising administering to a subject an effective amount of a fusion polypeptide of the invention. In a preferred aspect, the fusion polypeptide is substantially purified (e.g., substantially free from substances that limit its effect or produce undesired side-effects). The subject is preferably a mammal, and most preferably a human.

Various delivery systems are known and can be used to administer an agent of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Methods of introduction can be enteral or parenteral and include but are not limited to intradermal, intramuscular, intra-articular, intravenous, subcutaneous, intranasal, intraocular, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Administration can be acute or chronic (e.g. daily, weekly, monthly, etc.) or in combination with other agents. Pulmonary administration can also be employed, e.g., by use of an inhaler or nebulizer, and formulation with an aerosolizing agent.

In another embodiment, the active agent can be delivered in a vesicle, in particular a liposome, in a controlled release system, or in a pump. In another embodiment where the active agent of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see, for example, U.S. Pat. No.4,980,286), by direct injection, or by use of microparticle bombardment, or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination. Systemic expression may also be achieved by plasmid injection (intradermally or intramuscularly) and electroporation into cells.

In a specific embodiment, the pharmaceutical compositions of the invention are administered locally to an area in need of treatment; this may be achieved, for example, and not by way of limitation, by local infusion during surgery, topical application, e.g., by injection, by means of a catheter, or by means of an implant, the implant being of a porous, non-porous, or gelatinous material, including membranes, such as sialastic membranes, fibers, or commercial skin substitutes.

A composition useful in practicing the methods of the invention may be a liquid comprising an agent of the invention in solution, in suspension, or both. The term "solution/suspension" refers to a liquid composition where a first portion of the active agent is present in solution and a second portion of the active agent is present in particulate form, in suspension in a liquid matrix. A liquid composition also includes a gel. The liquid composition may be aqueous or in the form of an ointment.

In one embodiment, the pharmaceutical composition of the invention is a sustained release composition. Sustained release formulations for delivery of biologically active peptides are known to the art. For example, U.S. Pat. No. 6,740,634, herein specifically incorporated by reference in its entirety, describes a sustained-release formulation containing a hydroxynaphtoic acid salt of a biologically active substance and a biodegradable polymer. U.S. Pat. No. 6,699,500 herein specifically incorporated by reference in its entirety, discloses a sustained-release formulation capable of releasing a physiologically active substance over a period of at least 5 months.

Diagnostic and Screening Methods

The fusion polypeptides of the invention may be used diagnostically and/or in screening methods. For example, the fusion polypeptide may be used to monitor levels of interferon y during a clinical study to evaluate treatment efficacy. In another embodiment, the methods and compositions of the present invention are used to screen individuals for entry into a clinical study to identify individuals having, for example, too high or too low a level of interferon γ. The fusion polypeptides of the invention can be used in methods known in the art relating to the localization and activity of interferon γ, e.g., imaging, measuring levels thereof in appropriate physiological samples, in diagnostic methods, etc.

The fusion polypeptides of the invention may be used in in vivo and in vitro screening assays to quantify the amount of non-bound interferon γ present, e.g., for example, in a screening method to identify test agents able to decrease the expression of interferon γ. More generally, the fusion polypeptides of the invention may be used in any assay or process in which quantification and/or isolation of interferon γ is desired.

Pharmaceutical Compositions

The present invention also provides pharmaceutical compositions comprising a fusion polypeptide of the invention. Such compositions comprise a therapeutically effective amount of one or more fusion polypeptide(s), and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin.

The fusion polypeptide of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the fusion polypeptide that will be effective for its intended therapeutic use can be determined by standard clinical techniques based on the present description. In addition, in vitro assays may optionally be employed to help identify optimal dosage ranges. Generally, suitable dosage ranges for intravenous administration are generally about 0.02-10 milligrams active compound per kilogram body weight. Suitable dosage ranges for intranasal administration are generally about 0.01 pg/kg body weight to 10 mg/kg body weight. Effective doses may be extrapolated from dose-response curves derived from in vitro or animal model test systems. The amount of compound administered will, of course, be dependent on the subject being treated, on the subject's weight, the severity of the affliction, the manner of administration, and the judgment of the prescribing physician. The therapy may be repeated intermittently while symptoms are detectable or even when they are not detectable.

Cellular Transfection and Gene Therapy

The present invention encompasses the use of nucleic acids encoding the fusion polypeptides of the invention for transfection of cells in vitro and in vivo. These nucleic acids can be inserted into any of a number of well-known vectors for transfection of target cells and organisms. The nucleic acids are transfected into cells ex vivo and in vivo, through the interaction of the vector and the target cell facilitated by lipid mixes or electroporation. The compositions are administered (e.g., by injection into a muscle) to a subject in an amount sufficient to elicit a therapeutic response. An amount adequate to accomplish this is defined as "a therapeutically effective dose or amount."

In another aspect, the invention provides a method of reducing interferon γ levels in a human or other animal comprising transfecting a cell with a nucleic acid encoding a polypeptide of the invention, wherein the nucleic acid comprises an inducible promoter operably linked to the nucleic acid encoding the polypeptide. For gene therapy procedures in the treatment or prevention of human disease, see for example, Van Brunt (1998) Biotechnology 6:1149-1154.

EXAMPLES

The following example is put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Construction of Interferon γ-Binding Fusion Polypeptides

To create the interferon γ-binding fusion polypeptides hIFNγRα.hIFNγRβ.hFc (SEQ ID NO:7) nucleic acid encoding amino acids 1-239 (including signal sequence 1-17) of the human IFNγRα sequence (SEQ ID NO:2) and amino acids 28-246 of the human IFNγRβ sequence (SEQ ID NO:4) were ligated into an expression vector which contained the human Fc sequence, thus creating a fusion protein having the IFNγRα and IFNγRβ, and the hinge, CH2 and CH3 regions of human IgG1 from the N to C terminus. Molecules created encoded hIFNγR$\alpha_{(1\text{-}239)}$.hFc (SEQ ID NO:11), hIFNγ R$\alpha_{(1\text{-}239)}$. hIFNγRβ.hFc (SEQ ID NO:7), hIFNγR$\alpha_{(1\text{-}239)}$. hIFNγRβ(C174S).hFc (SEQ ID NO:9), hIFNγR$\alpha_{(1\text{-}239)}$. TG.hIFNγRβ.SG.hFc (SEQ ID NO:13), hIFNγR$\alpha_{(1\text{-}239)}$. TG.hIFNγRβ(C174S).SG.hFc (SEQ ID NO:15). All sequences were verified by standard molecular biology techniques. The appropriate coding sequence was subcloned into a eukaryotic expression vector using standard molecular biology techniques.

The interferon γ-binding fusion polypeptide variants hIFNγRα.hIFNγRβ(C174S).hFc (SEQ ID NO:9) and hIFNγR$\alpha_{(1\text{-}239)}$.TG.hIFNγRβ(C174S).SG.hFc (SEQ ID NO:15) were created by site-directed mutagenesis of the parent fusion polypeptide using techniques known to the art, and confirmed by sequencing.

Example 2

Determination of Interferon γ Binding Affinity

The affinity of the interferon γ-binding fusion polypeptides for human interferon γ was measured using a BIAcore 2000™ or BIAcore 3000™, as described in WO 00/75319, herein specifically incorporated by reference in its entirety. Briefly, the IFNγ-specific polypeptides were produced as small-scale supernatants by transiently transfecting CHO cells, using Lipofectamine/LIPO Plus® (Life Technologies), with DNA constructs encoding the proteins. Supernatants were collected after 72 hours and protein expression was measured by Western blotting with anti-human Fc HRP-conjugated antibody (Promega) and visualized by ECL (Pierce). Briefly, $5.4\times10^5$ CHOK1 cells per well of a 6 well tissue culture dish were transfected using 1 μg of DNA and 5 μl of lipofectamine in OptiMEM™ (Gibco). After 12 h the cells were washed with OptiMEM™ and 2 ml of CHO serum free medium (Gibco) was added. After 60 h and 72 h the media was collected and centrifuged to remove cellular debris. Expression levels for the various interferon γ-binding fusion polypeptides are shown in Table 1. For the BiaCore™ analysis, the IFNγ-binding fusion polypeptides from the transiently transfected CHO supernatants were captured onto the chip surface using anti-human Fc antibodies. Various concentrations of human IFNγ are injected over the surface and the time course of association and dissociation are monitored. Kinetic analyses using BIA evaluation software were performed to obtain the association and dissociation rate constants. The results obtained for the dimeric constructs are summarized in Table 1. The Kd of control IFNγRα(1-239)-Fc was $6.0\times10^{-9}$ M whereas the Kd for hIFNγRα.hIFNγRβ.hFc was $1.3\times10^{-11}$ M, an approximately 60-fold improvement in affinity. hIFNγRβ.SG.hFc showed no ability to bind IFNγ. Only R1-R2-Fc constructs (with or without C174S) behaved as traps, exhibiting an affinity improvement from the individual component affinities. Unlike many receptor-based fusion protein traps, other configurations such as R2-R1-Fc or R1-Fc-R2 were poor inhibitors, having a Kd values greater than 10 nM. Molecules having N-terminal deletions in R1 (pCTR 2890, 2891, 2892, 2847, 2982, 2900, 2901, 2982) expressed poorly or exhibited reduced the affinity for IFNγ. The presence or absence of linkers did not affect the affinity of the molecules.

Example 3

Determination of IFNγ IC50 Values Using Luciferase Bioassays

IFNγ Inhibition assay. The HEK293/ISRE or GAS-luciferase bioassay was used to determine the ability of the IFNγ-specific polypeptides of the invention to block the activity of human IFNγ. Human embryonic kidney 293 (HEK293) cells, were transiently transfected with an ISRE- or GAS-luciferase reporter plasmids. By placing an ISRE or GAS promoter element upstream of the luciferase gene one can monitor IFNγ activity in cells. For the assay, transiently transfected ISRE or GAS-luciferase HEK293 cells were suspended at $1.25\times10^5$ cells per ml in medium and 0.08 ml of cells plated (10,000 cells per well) into the wells of a 96 well tissue culture plate. Plates were incubated for ~16 hours at 37° C. in a humidified 5% $CO_2$ incubator. IFNγ-specific polypeptides and recombinant human IFNγ at varying doses were separately mixed in a 96 well tissue culture dish. 0.026 ml of each of these mixtures were then added to the 96 well plate (IFNγ-specific polypeptides added first) containing the ISRE or GAS-luciferase cells such that the final concentration of IFNγ is 4 pM and the final concentrations of the IFNγ-specific polypeptide ranged from 0.017 pM to 30 nM. Control wells contain no IFNγ-specific polypeptide. Plates were incubated at 37° C. for 6 hours in a humidified 5% $CO_2$ incubator. After 6 hours, the plates were equilibrated to room temperature for ~30 minutes and 130 μl of Steady-Glo® luciferase substrate (Promega) was added. Plates were incubated at room temperature for ~10 minutes and then read on a Victor™ multilabel counter (Luminescence 1 sec/well). IC50s were measured which is a 50% reduction in IFNγ stimulated activity, then determined with a 4 parameter fit analysis using Prism™ software (Graph Pad). Table 1 shows the bioassay IC50 values of the IFNγ polypeptides produced as CHO transient supernatants, whose concentrations were determined by Western blot analysis using PAGE under reducing conditions. IC50 values also show that only the R1-R2-Fc construct (with or without C174S) shows an enhanced ability to block IFN. The IC50 values in the ISRE and GAS luciferase assays for hIFNγRα.hIFNγRβ.hFc and hIFNγRα.hIFNγRβ (C174S).hFc are 1-5×$10^{-10}$M, whereas the individual receptor constructs, hIFNγRα$_{(1-239)}$.SG.hFc or hIFNγRβ.SG.hFc, gave an IC50 value of 6-8×$10^{-9}$ M or undetectable blocking, respectively.

TABLE 1

| PCTR | Constructs | Expression ug/ml | BiaCore ™ (M) | IC50 (M) ISRE | IC50 (M) GAS |
|---|---|---|---|---|---|
| | IFNγRα.Fc constructs | | | | |
| 2852 | hIFNγRα$_{(1-246)}$.SG.hFc | n/a | | | |
| 2827 | hIFNγRα$_{(1-239)}$.SG.hFc | 15 | 6.00E−09 | 6.20E−09 | 7.90E−09 |
| | Configuration Variants | | | | |
| 2842 | hIFNγRα$_{(1-239)}$.TG.hIFNγRβ.SG.hFc | 12 | 1.29E−11 | 0.72E−10 | 2.02E−10 |
| | | | | 1.0E−10 | 3.8E−10 |
| 2987 | hIFNγRα$_{(1-239)}$.hIFNγRβ.hFc | | | | |
| 2845 | hIFNγRα$_{(1-239)}$.TG.hIFNγRβ(C174S).SG.hFc | 10 | | 1.18E−10 | 4E−10 |
| | | | | 1.54E−10 | 4.52E−10 |
| 2988 | hIFNγRα$_{(1-239)}$.hIFNγRβ(C174S).hFc | | | | |
| 2843 | hIFNγRβ.TG.HifnγRα$_{(1-239)}$.SG.hFc | 15 | No binding | 1.46E−08 | 9.80E−09 |
| 2844 | hIFNγRα$_{(1-239)}$.TG.hFc.ARA.hIFNγRβ | 15 | | 8.00E−07 | 1.60E−08 |
| 2843 | hIFNγRβ.TG.hFc.ARA.hIFNγRα$_{(1-239)}$ | n/a | | | |
| | hIFNγRβ.Fc trap constructs | | | | |
| 2828 | hIFNγRβ.SG.hFc | 15 | No binding | | |
| 2848 | hIFNγRβ(C174S).SG.hFc | 15 | No Binding | | |
| | hIFNγRα.Fc deletion constructs | | | | |
| 2890 | hIFNγRα$_{(23-239)}$.SG.hFc | 2 | | 2.57E−09 | 4.60E−09 |
| 2891 | hIFNγRα$_{(24-239)}$.SG.hFc | 10 | | 1.20E−08 | 2.10E−08 |
| 2892 | hIFNγRα$_{(29-239)}$.SG.hFc | n/a | | | |
| 2847 | hIFNγRα$_{(33-239)}$.SG.hFc | 1 | | | |
| 2982 | hIFNγRα$_{(1-239\Delta 173-180)}$.SG.hFc | n/a | | | |
| 2900 | hIFNγRα$_{(42-239)}$.SG.hFc | n/a | | | |
| 2901 | hIFNγRα$_{(52-239)}$.SG.hFc | n/a | | | |
| | R1 deletion constructs in different configurations | | | | |
| 2959 | hIFNγRα$_{(23-239)}$.TG.hIFNγRβ.SG.hFc | 4 | | 5.30E−11 | 1.90E−10 |
| 2960 | hIFNγRα$_{(24-239)}$.TG.hIFNγRβ.SG.hFc | 2 | | 1.30E−09 | 3.20E−09 |
| 2851 | hIFNγRα$_{(33-239)}$.TG.hIFNγRβ.SG.hFc | 2 | | 2.40E−07 | 1.30E−08 |
| 2962 | hIFNγRα$_{(23-239)}$.TG.hFc.ARA.hIFNγRβ | n/a | | 7.90E−10 | 1.00E−09 |
| 2961 | hIFNγRα$_{(24-239)}$.TG.hFc.ARA.hIFNγRβ | 10 | | 6.00E−09 | 1.10E−08 |
| 2951 | hIFNγRα$_{(33-239)}$.TG.hFc.ARA.hIFNγRβ | <1 | | | |
| | Mouse constructs | | | | |
| 2983 | mIFNγRα.mFc | n/a | | | |
| 2984 | mIFNγRβ.mFc | n/a | | | |
| 3002 | mIFNγRα.TG.mIFNγRβ.SG.mFc | n/a | | | |

We claim:

1. A fusion protein comprising the amino acid sequence of SEQ ID NO:7 or 9.

2. A multimeric protein comprising two of the fusion proteins of claim 1.

3. A fusion protein comprising the amino acid sequence of SEQ ID NO:13 or 15.

4. A multimeric protein comprising two of the fusion proteins of claim 3.

5. A fusion protein comprising R1,R2 and F in the N-terminus direction, and optionally a spacer sequence between R1 and R2, or R2 and F, or both, wherein R1 comprising amino acids 1-239 of SEQ ID NO:2;

R2 comprising amino acids 28-246 of SEQ ID NO:4, wherein cysteine 174 of SEQ ID NO:4 is optionally changed to a different amino acid; and F is a multimerizing component selected from the group consisting of the Fc domain if IgG and a heavy chain of IgG; and wherein said fusion protein has an IC50 of 1-5×$10^{-10}$ M in inhibiting the activity of human IFNγ as measured by a luciferase assay, or a Kd of about 1×$10^{-11}$ M for human IFNγ as measured by surface plasmon resonance, or both.

6. A nucleic acid molecule encoding the fusion protein of claim 5.

7. A vector comprising the nucleic acid molecule of claim 6.

8. A host-vector system comprising the vector of claim 7, in a suitable host call.

9. A method of producing a fusion polypeptide, comprising culturing the host-vector system of claim 8 under conditions suitable for expression of the protein from the host call, and recovering the polypeptide so produced.

10. A multimeric protein comprising two of the fusion protein of claim 5.

* * * * *